US00PP13168P2

(12) United States Plant Patent
Odom

(10) Patent No.: US PP13,168 P2
(45) Date of Patent: Nov. 5, 2002

(54) *EUONYMUS ALATUS* PLANT NAMED 'ODOM'

(75) Inventor: Jack W. Odom, Morrison, TN (US)

(73) Assignee: Odom Nursery Company, Morrison, TN (US)

( * ) Notice: Subject to any disclaimer, the term of this patent is extended or adjusted under 35 U.S.C. 154(b) by 0 days.

(21) Appl. No.: 09/609,589

(22) Filed: Jun. 30, 2000

(51) Int. Cl.[7] ..... A01H 5/00
(52) U.S. Cl. ..... Plt./246
(58) Field of Search ..... Plt./246, 226

*Primary Examiner*—Bruce R. Campell
*Assistant Examiner*—June Hwu
(74) *Attorney, Agent, or Firm*—Klarquist Sparkman, LLP

(57) ABSTRACT

A burning bush named 'ODOM' having a short dense habit and slow growth rate.

3 Drawing Sheets

DESCRIPTION

The present invention relates to a new and distinct variety of *Euonymus alatus,* burning bush, which has been given the varietal name 'ODOM.'

I discovered the original plant of my new variety growing in a ball hole from which a burning bush had been previously removed. My new variety is believed to be either a seedling sport or a root sport. The original plant was discovered growing outdoors in a cultivated area in the corner of a nursery block in McMinnville, Tenn. My attention was drawn to the plant because of its slow growth and compact, diminutive size. My new variety is particularly useful in landscape settings where small, slowing growing bushes are desired.

'ODOM' is an attractive plant that exhibits a slow rate of growth compared to other varieties of burning bush, particularly when grown under nursery and container conditions. Three-year-old 'ODOM' plants have only grown to a height of 10" to 12" in containers and new beds while maintaining dense branches and leaves. When the original plant of my variety was 12 years old, it was only 30" high and 4' wide. The growth habit is dense and of a desirable rotund and slightly flattened shape. The dense habit is due primarily to densely spaced nodes and leaves and also to many multiple breaks from new growth shoots from each season. Insofar as I have observed as of this time, leaves are typically smaller than other burning bush varieties but have the same color and shape as the species. The leaves also tend to hold longer into the fall season when compared to other varieties of burning bush plants I have observed growing in the McMinnville, Tenn. area. Flowers and fruits of my new variety, insofar as I have observed as of this time, are the same as other varieties which I have observed.

The morphological characteristics of the variety 'ODOM' described above serve to distinguish 'ODOM' from other varieties of burning bush plants of which I am aware. For example, other known varieties of burning bush growing in McMinnville, Tenn., typically reach 10' to 12' in height which limits their utility as a foundation landscape plant unless they are heavily pruned.

The new variety 'ODOM' has been asexually reproduced at my direction from cuttings in McMinnville, Tenn., and observation of the resulting plants that have been grown in a nursery in McMinnville, Tenn., has proven that the characteristics of my new variety are stable. Furthermore, these observations have confirmed that my new variety presents a new and improved compact growing variety of burning bush plant.

More specifically, my new variety has been asexually reproduced during June through October from 4 to 6 inch long wood cuttings that are treated using a quick dip of 1000–3000 ppm indole 3 butyric acid, napthalene acetic acid. Cuttings have been propagated in a 50% peat/50% perlite mix and straight sand with near 100% success. Typically rooting occurs in 4–12 weeks. All plants of my variety which have been asexually propogated have maintained the characteristic compact, diminutive size and slow growth exhibited by the original plant. Thus, my new variety is stable.

In summary, the new variety 'ODOM' is distinguishable from all other varieties of burning bush of which I am aware because it displays a combination of unique characteristics. These characteristics have been stably expressed through several generations of cuttings and, moreover, these characteristics render the plant useful for planting in various landscapes. The following combination of characteristics distinguish the 'ODOM' variety: 1) low growth; 2) dense compact habit; 3) new growth in McMinnville, Tenn., seldom exceeding 6" per season; and 4) leaves that hold longer in the fall than typical of the species observed to date.

The following is a detailed description of the invention based on plants grown in a nursery in McMinnville, Tenn. Color descriptions and other terminology are used herein in accordance with ordinary dictionary significance unless otherwise noted with reference to The Royal Horticultural Society Colour Chart (R.H.S.) It should be noted that color does vary with time of year, lighting conditions, and soil and nutrient conditions. For example, leaf colors tend to be brighter green if the plants are grown in soil with greater nitrogen concentrations, and to be more yellow when grown in soil containing lesser amounts of nitrogen.

BRIEF DESCRIPTION OF THE FIGURES

The accompanying photographs depict the size, color, and branching structure of my new variety 'ODOM'.

THE PLANT

Figure 1:
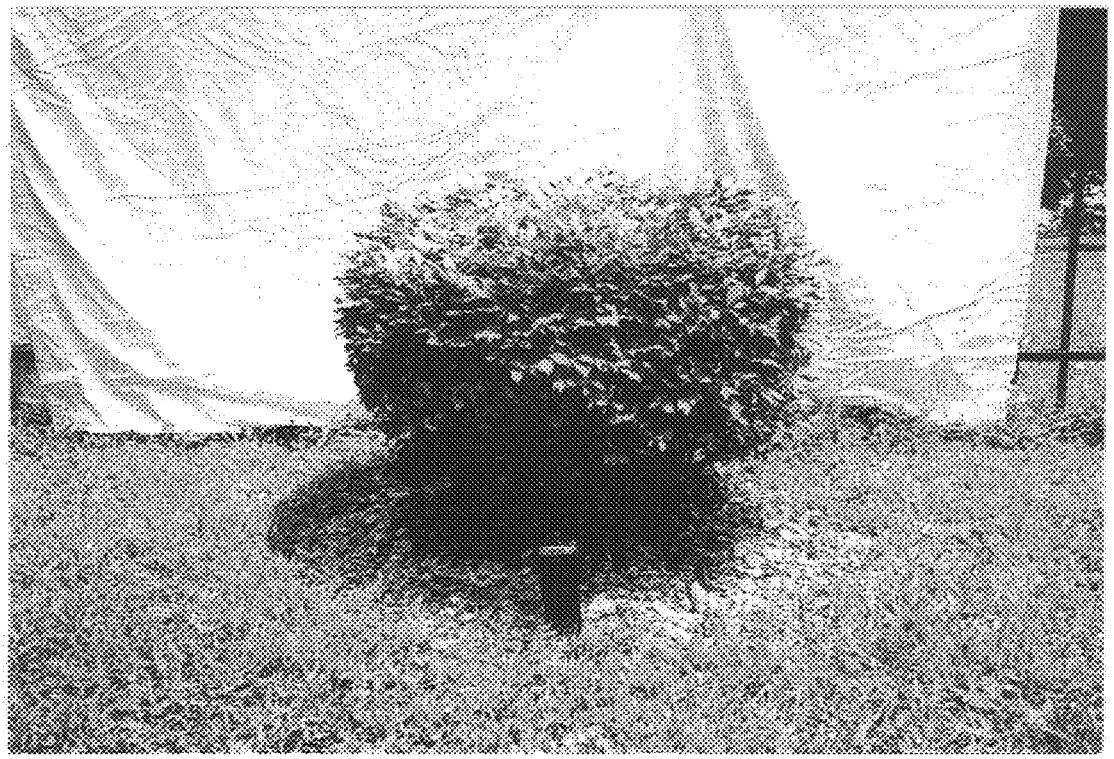
FIG. 1 is a photograph of the original 'ODOM' plant, depicting its growth and habit.
Figure 2:
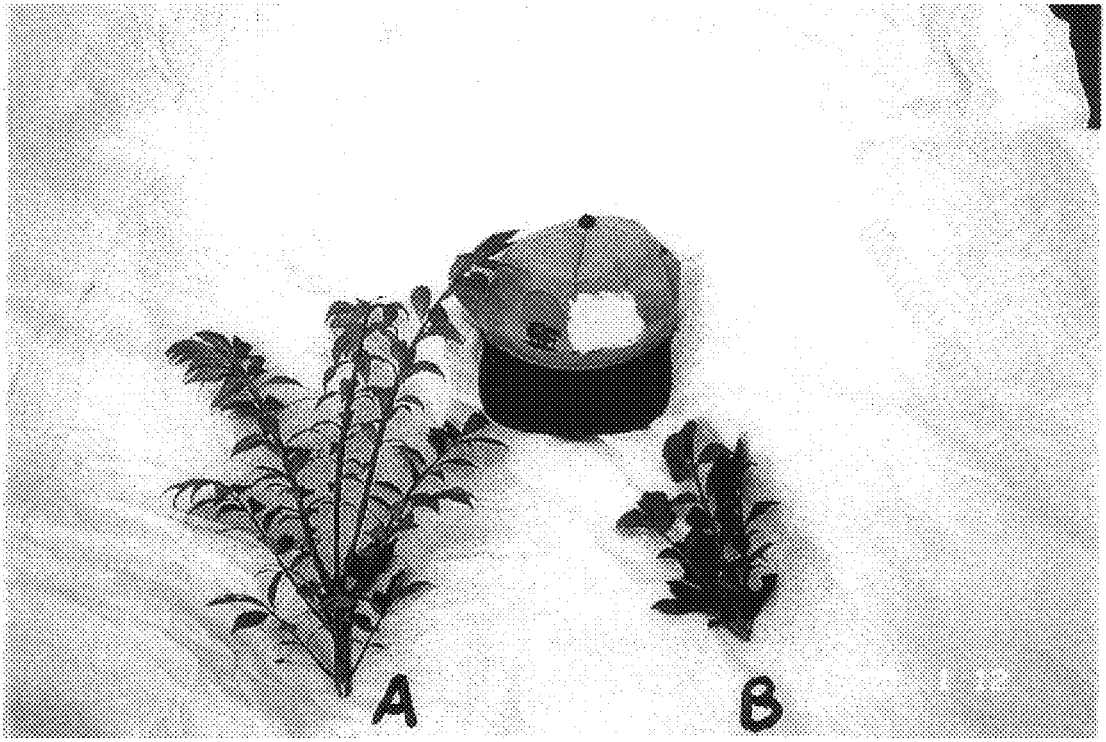
FIG. 2 is a photograph comparing one year's growth from the 'Compacta' variety of burning bush (A)(unpatented), which exhibits typical growth, to one year's growth from the 'ODOM' variety (B).
Figure 3:
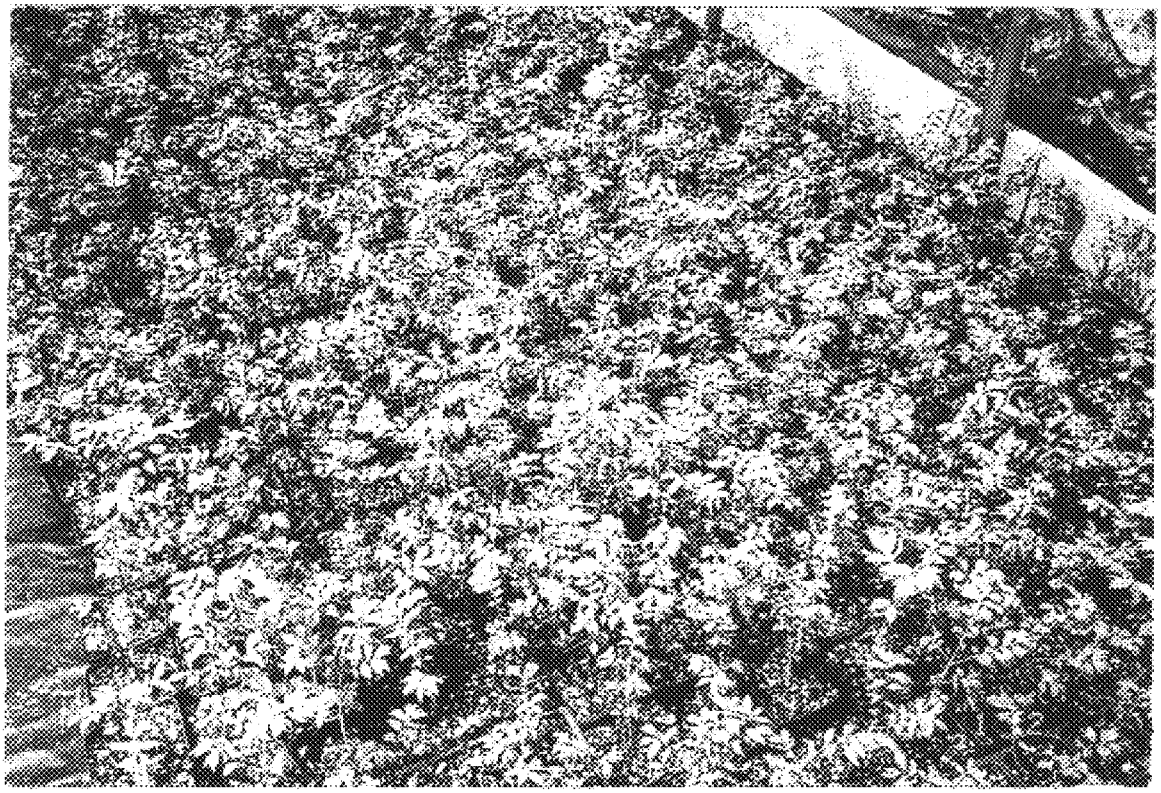
FIG. 3 is a photograph of 2-year-old 'ODOM' plants in containers.

The following is a description of plants of the new variety growing in McMinnville, Tenn.

Parentage: Unknown. Believed to be either a root sport or a seedling sport.

Propogation: Holds to distinguishing characteristics through succeeding asexual propagation by cuttings.

Bush:

*Bush shape*.—Rotund and slightly flattened.

*Bush size*.—Mature size unknown. Original plant at 12 years old was 30" high and 4' wide.

*Bush growth*.—One or more suckers often grow from at or about ground level and enhances the apparent density of the plant.

Branches:

*Branching pattern*.—Dense with an internode length ranging from 1" to 6".

*New branches* (*stems*).—Green (RHS 137A) in color, measuring 1/16" to 1/4" in diameter; glabrous; primary new growth branches often have cork textured protuberances which can be about as long as the new growth branches.

*Mature* (*Three-year old*) *branches* (*stems*).—Grey-green (RHS 197A) in color; corky and rough.

Leaves:

*Leaf size*.—About 1" to 2" long and 1/2" to 3/4" wide.

*Upper surface*.—Yellow-green (RHS 147A), changing to red (RHS 46A) in the fall; glabrous.

*Lower surface*.—Yellow-green (RHS 146A); glabrous.

*Arrangement*.—Opposite to subopposite.

*Margin*.—Finely serrate.

*Shape*.—Elliptic to slightly obovate.

*Petiole*.—About 1/8" long and yellow-green (RHS 144B) in color.

*Apex*.—Acute.

*Base*.—Acute.

Flowers: About 3/16" long and 3/16" wide; not ornamental or showy; perfect, with four rounded petals that are yellow-green (RHS 153D) in color and four short stamens about 1/16 long with yellow-orange (RHS 14A) anthers attached to a broad, flat, yellow-green (RHS 153C) disk; flowers mature in May to June.

*Disease resistance*.—Twig blight observed in very wet conditions.

*Insect resistance*.—Scale has been observed on a few plants, but no major pest infestations have been observed.

*Hardiness*.—Full range unknown, observed primarily in hardiness Zone 6. Expected to be at least as hardy as the species, hardiness Zones 4–8 and possibly 9.

*Seeds*.—About 1/4" to 1/3" long; covered with an oranged-red (RHS 33A) aril.

I claim:

1. A new and distinct variety of burning bush plant substantially as herein shown and described, characterized particularly as to novelty by its slow growth rate and unique, dense habit.

* * * * *

UNITED STATES PATENT AND TRADEMARK OFFICE

CERTIFICATE OF CORRECTION

PATENT NO. : PP 13,168 P2
DATED : November 5, 2002
INVENTOR(S) : Jack W. Odom

It is certified that error appears in the above-identified patent and that said Letters Patent is hereby corrected as shown below:

Column 4,
Line 14, change "1/16" to -- 1/16" --
Line 26, change "oranged-red" to -- orange-red --

Signed and Sealed this

Twenty-third Day of September, 2003

JAMES E. ROGAN
*Director of the United States Patent and Trademark Office*